United States Patent
Fahey et al.

(10) Patent No.: US 12,329,433 B2
(45) Date of Patent: Jun. 17, 2025

(54) SYSTEMS, DEVICES, AND METHODS FOR TREATMENT OF NASAL DISORDERS

(71) Applicant: Arrinex, Inc., Redwood City, CA (US)

(72) Inventors: Brian Fahey, Menlo Park, CA (US); William Jason Fox, San Mateo, CA (US); Mojgan Saadat, Atherton, CA (US); Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 1155 days.

(21) Appl. No.: 17/251,939

(22) PCT Filed: Jun. 26, 2019

(86) PCT No.: PCT/US2019/039199
§ 371 (c)(1),
(2) Date: Dec. 14, 2020

(87) PCT Pub. No.: WO2020/006051
PCT Pub. Date: Jan. 2, 2020

(65) Prior Publication Data
US 2021/0369320 A1     Dec. 2, 2021

Related U.S. Application Data

(60) Provisional application No. 62/690,247, filed on Jun. 26, 2018.

(51) Int. Cl.
*A61B 18/18* (2006.01)
*A61B 18/02* (2006.01)
*A61B 18/00* (2006.01)

(52) U.S. Cl.
CPC .... *A61B 18/02* (2013.01); *A61B 2018/00214* (2013.01); *A61B 2018/00327* (2013.01);
(Continued)

(58) Field of Classification Search
CPC .......... A61B 18/02; A61B 2018/00041; A61B 2018/00196; A61B 2018/00214;
(Continued)

(56) References Cited

U.S. PATENT DOCUMENTS 3,901,241 A    8/1975  Allen, Jr.
5,843,077 A    12/1998 Edwards
(Continued)

FOREIGN PATENT DOCUMENTS

CN    108024711 A      5/2018
EP    2 797 516 B9     11/2014
WO    2016/183337 A2   11/2016

OTHER PUBLICATIONS

Extended European Search Report issued by the European Patent Office in Application No. 23220526.0 dated Apr. 26, 2024.
(Continued)

*Primary Examiner* — Michael F Peffley
*Assistant Examiner* — Amanda L Zink
(74) *Attorney, Agent, or Firm* — McDonnell Boehnen Hulbert & Berghoff LLP

(57) ABSTRACT

Systems, devices, and methods involve ablation of tissue to treat rhinitis and/or other nasal conditions. Implementations allow treatment of tissue in the confined space of the nasal cavity. Additionally, implementations allow targeted treatment tissue to be ablated, while protecting other non-treatment tissue from unintentional collateral effects that might be produced by the ablation. According to an example implementation, an approach for treating a nasal condition includes advancing a probe into a nasal cavity, the probe including a shaft and a cryotherapy element coupled to the shaft. The approach also includes cryogenically cooling a target treatment site with the cryotherapy element to treat at least one nasal nerve. Additionally, the approach includes
(Continued)

transmitting a focused ultrasound beam to a target heating site to increase a temperature tissue at the target heating site.

21 Claims, 10 Drawing Sheets

(52) U.S. Cl.
CPC ............ *A61B 2018/00404* (2013.01); *A61B 2018/00434* (2013.01); *A61B 2018/00583* (2013.01); *A61B 2018/00815* (2013.01); *A61B 2018/00821* (2013.01); *A61B 2018/00994* (2013.01)

(58) Field of Classification Search
CPC .......... A61B 2018/00327; A61B 2018/00404; A61B 2018/00434; A61B 2018/00577; A61B 2018/00583; A61B 2018/00791; A61B 2018/00815; A61B 2018/00821; A61B 2018/00994; A61B 2090/0463; A61B 2090/378
See application file for complete search history.

(56) References Cited

U.S. PATENT DOCUMENTS

| | | | |
|---|---|---|---|
| 6,063,079 A | 5/2000 | Hovda et al. | |
| 6,361,531 B1* | 3/2002 | Hissong | A61N 7/02 606/78 |
| 6,378,525 B1 | 4/2002 | Beyar et al. | |
| 2007/0167776 A1* | 7/2007 | Kochavi | A61B 8/546 600/459 |
| 2007/0225781 A1* | 9/2007 | Saadat | A61F 7/12 607/105 |
| 2008/0027423 A1 | 1/2008 | Choi et al. | |
| 2012/0184879 A1* | 7/2012 | Tanis | A61N 7/00 601/2 |
| 2012/0323227 A1 | 12/2012 | Wolf et al. | |
| 2014/0330124 A1 | 11/2014 | Carol | |
| 2015/0164571 A1 | 6/2015 | Saadat | |
| 2016/0045277 A1* | 2/2016 | Lin | A61B 18/02 604/93.01 |
| 2016/0206373 A1 | 7/2016 | Chen et al. | |
| 2016/0287334 A1 | 10/2016 | Grant et al. | |
| 2016/0331459 A1* | 11/2016 | Townley | A61N 1/403 |
| 2018/0344411 A1* | 12/2018 | Fahey | A61B 18/06 |

OTHER PUBLICATIONS

Examination Report No. 1 issued by the Australian Patent Office in Application No. 2022231648 dated Jan. 15, 2024.
International Search Report mailed on Oct. 8, 2019, issued in connection with International Application No. PCT/US2019/039199, filed on Jun. 26, 2019, 5 pages.
Written Opinion mailed on Oct. 8, 2019, issued in connection with International Application No. PCT/US2019/039199, filed on Jun. 26, 2019, 8 pages.
Notice of Completing Formalities for Patent Registration issued by the Chinese Patent Office in Application No. 201980043227.5 dated Jun. 25, 2024.

* cited by examiner

SYSTEMS, DEVICES, AND METHODS FOR TREATMENT OF NASAL DISORDERS

CROSS-REFERENCE TO RELATED APPLICATION(S)

The present application is the US national phase under 35 U.S.C. § 371 of International Application No. PCT/US2019/039199, filed Jun. 26, 2019, which claims priority to, and the benefit of, U.S. Provisional Patent Application No. 62/690,247, filed Jun. 26, 2018, the contents of each of which are incorporated entirely herein by reference.

BACKGROUND

Field

The present disclosure is generally related to systems, devices, and methods for treatment of nasal disorders, and is more particularly related to ablative treatments for rhinitis and/or other nasal conditions.

Description of Related Art

Rhinitis is defined as inflammation of the membranes lining the nose, characterized by nasal symptoms including itching, rhinorrhea, and/or nasal congestion. Chronic rhinitis affects tens of millions of people in the United States and leads a significant number of people to seek medical care. Medical treatment has been shown to have limited benefits for chronic rhinitis sufferers. Moreover, up to 20% of patients may be refractory.

SUMMARY

Aspects of the present disclosure relate to ablation of tissue to treat rhinitis and/or other nasal conditions. Implementations allow treatment of tissue in the confined space of the nasal cavity, which may be challenging to access and navigate. Additionally, implementations allow targeted treatment tissue to be ablated, while protecting other non-targeted tissue(s) (i.e., non-treatment tissues) from collateral effects that might be produced by the ablation. In particular, implementations may employ a probe to cryoablate the targeted treatment tissue within the nasal cavity, but protect the non-treatment tissue from the damaging effects of cold temperature produced during cryoablation.

According to an example implementation, a method for treating a nasal condition includes advancing a probe into a nasal cavity, the probe including a shaft and a cryotherapy element coupled to the shaft. The method includes cryogenically cooling a target treatment site with the cryotherapy element to treat at least one nasal nerve. The method includes transmitting a focused ultrasound beam to a target heating site to increase a tissue temperature at the target heating site.

According to an example implementation, a method for treating rhinitis, the method includes advancing a probe into a nasal cavity, the probe including a shaft and a cryotherapy element coupled to the shaft. The method includes cryogenically cooling a target treatment site with the cryotherapy element to ablate at least one nasal nerve. The method includes emitting a laser beam to a target heating site to increase a tissue temperature at the target heating site.

According to an example implementation, a method for treating rhinitis includes advancing a heated body into a mouth, wherein the heated body has an initial temperature in a range between 37 and 45 degrees Celsius. The method includes positioning the heated body proximate to a palate to increase a temperature of a target heating site. The method includes advancing a probe into a nasal cavity, the probe including a shaft and a cryotherapy element coupled to the shaft. The method includes cryogenically cooling a target treatment site with the cryotherapy element to ablate or otherwise modify at least one nasal nerve.

According to an example implementation, a method for cryogenically ablating upper airway mucosa within the nasal cavity includes advancing a probe into a nasal cavity, the probe comprising an elongated shaft and a cryotherapy element coupled to the shaft. The method includes advancing at least one warming probe into at least one of a nasal cavity or an oral cavity. The method includes cryogenically cooling a target treatment site with the cryotherapy element while warming tissue superior, inferior, anterior, posterior, lateral to, and/or medial to the target treatment site with the at least one warming probe to ablate at least one nasal nerve.

According to an example implementation, a system for treating a nasal condition includes a probe including a shaft and a cryotherapy element coupled to the shaft, wherein the probe is configured to be advanced into a nasal cavity and to cryogenically cool a target treatment site with the cryotherapy element to treat at least one nasal nerve. The system includes an ultrasound transducer assembly configured to transmit a focused ultrasound beam to a target heating site to increase a temperature of cooled tissue at the target heating site.

According to an example implementation, a system for treating rhinitis includes a probe including a shaft, a laser assembly coupled to the shaft, and a cryotherapy element coupled to the shaft. The probe is configured to be advanced into a nasal cavity and cryogenically cool a target treatment site with the cryotherapy element to treat at least one nasal nerve, and configured to emit a laser beam to a target heating site to increase a temperature of cooled tissue at the target heating site.

According to an example implementation, a system for treating rhinitis includes a heated body configured to be positioned in a mouth proximate to a palate with an initial temperature in a range between 37 and 45 degrees Celsius to increase a temperature of a target heating site. The system includes a probe comprising a shaft and a cryotherapy element coupled to the shaft. The probe is configured to be advanced into a nasal cavity and cryogenically cool a target treatment site, after the heated body is positioned in the mouth, with the cryotherapy element to treat at least one nasal nerve.

According to an example implementation, a system for cryogenically ablating upper airway mucosa within the nasal cavity includes a probe comprising a shaft and a cryotherapy element coupled to the shaft. The probe is configured to be advanced into a nasal cavity and cryogenically cool a target treatment site with the cryotherapy element to treat at least one nasal nerve. The system includes a warming probe configured to be inserted into at least one of a nasal cavity and an oral cavity to warm tissue superior, inferior, anterior, posterior, lateral to, and/or medial to the target treatment site.

BRIEF DESCRIPTION OF THE DRAWINGS

Further details and aspects of various implementations will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1B:
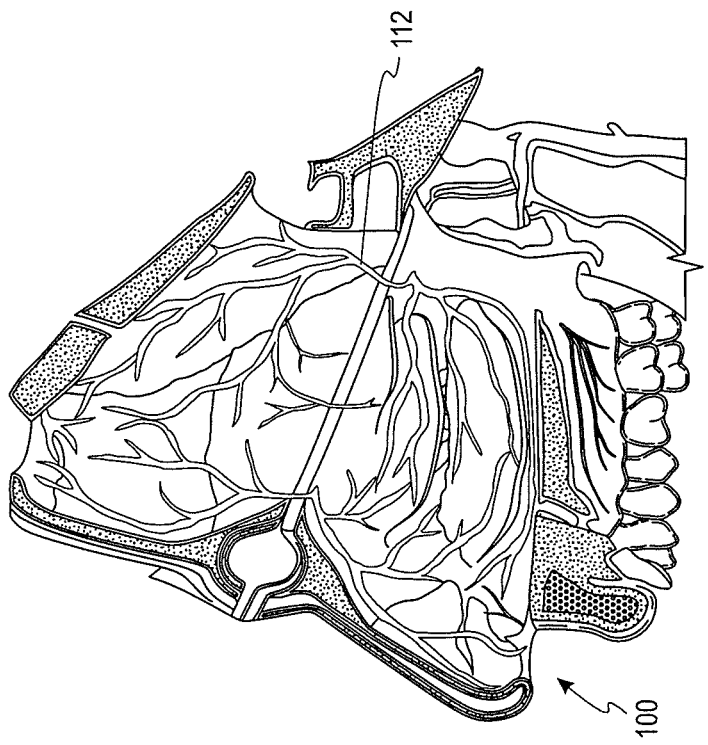
FIG. 1B illustrates aspects of the anatomy of a nose, including blood vessels in the lateral wall of a nasal cavity.
Figure 1A:
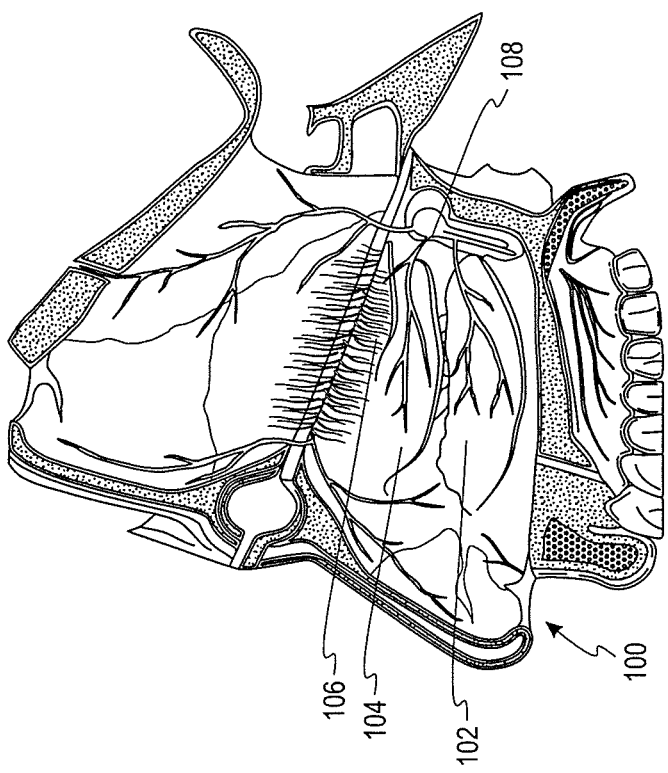
FIG. 1A illustrates aspects of the anatomy of a nose, including nerves in the lateral wall of a nasal cavity.

FIGS. 1A-1B illustrate aspects of the anatomy of a nose. FIG. 1A illustrates nerves in a lateral wall of a nasal cavity 100. Three bony prominences reside on the lateral wall on each side of the nasal cavity 100: an inferior turbinate 102, a middle turbinate 104, and a superior turbinate 106. Posterior nasal nerves (PNN) 108 are generally located in a posterior aspect of the nasal cavity 100, with main branches located proximal to a posterior aspect of the middle turbinate 104. The PNN 108 originate from the sphenopalatine ganglion and are responsible for the parasympathetic control of the nasal mucosa including mucosa covering the turbinates. Other accessory posterior nasal nerves (APNN) (not shown) originate from the greater palatine nerve or from the bony plate underneath the mucosa and course through the mucosa directly over the palatine canal.

The PNN 108 as well as the APNN are desirable targets for ablation for the treatment of rhinitis and other nasal conditions. Ablative treatments induce temperature changes to scar or destroy tissue in target regions. Ablation may be achieved by applying heat with radiofrequency, laser, microwave, high intensity focused ultrasound (HIFU), or resistive heating. Alternatively, ablation may be achieved by applying cooling energy in a process also known as cryoablation. Cryoablation in the nasal cavity may be performed under endoscopic guidance that provides the user with visualization capability to assist with navigation within the relatively confined space.

Ablation of the PNN 108 and the APNN in patients with chronic rhinitis improves symptoms while avoiding the morbidities associated with vidian neurectomy. In particular, the ablation interrupts at least a portion of the autonomic innervation to the nasal mucosa and can reduce the hypersensitivity and axon reflexes of the nasal mucosa. Although ablation of the PNN 108 and the APNN is a less invasive procedure with fewer side effects than other surgical methods for treating rhinitis, complications can occur if other regions in the nasal cavity 100, for example regions containing large blood vessels, are impacted or modulated during the ablation.

FIG. 1B illustrates blood vessels in the lateral wall of the nasal cavity 100. In particular, FIG. 1B shows a sphenopalatine artery (SPA) 112 which located near the PNN 108 as correspondingly shown in FIG. 1A. The PNN 108 generally follows the SPA 112. As such, during ablation of the PNN 108, unintentional collateral effects may be experienced by the SPA 112. Unintentional collateral effects may also be experienced by other structures within the palatine canal. Such collateral effects may lead to excessive bleeding, patient discomfort during and/or post procedure, and/or other injury to the patient. In some cases, an excessive nose bleed may require subsequent surgical treatment or intervention. The SPA and structures within the palatine canal represent regions that should be insulated from the thermal effects associated with the ablation of the PNN 108 and the APNN.

Implementations according to the present disclosure provide systems, devices, and methods for accessing and treating tissue in the small, confined space of the nasal cavity. In particular, to treat rhinitis, implementations can ablate tissue in targeted treatment regions in the nasal cavity, including the PNN 108 and the APNN, while protecting tissue in other non-treatment regions, such as the SPA 112, from unintentional collateral effects resulting from the ablation. (As used herein, non-treatment regions refer to regions of tissue that are not targeted for ablative treatment. Such non-treatment regions may include sensitive tissue that is preferably protected from unintentional collateral effects from an ablative treatment.)

Figure 2:
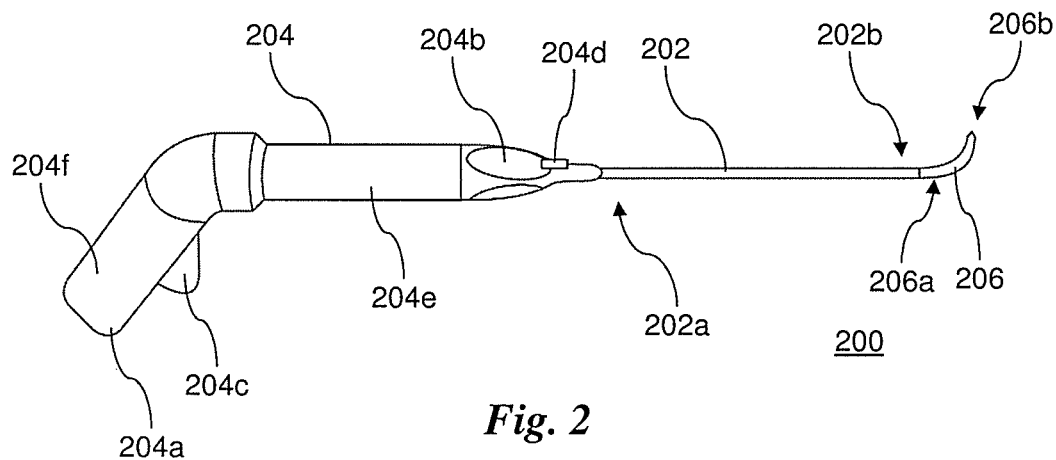
FIG. 2 illustrates an example cryoablation probe configured to cryoablate targeted treatment regions within a nasal cavity.

FIG. 2 illustrates an example cryoablation probe 200 configured to ablate targeted treatment regions within a nasal cavity by applying a cryogen (cryogenic cooling). The cryoablation probe 200 includes a shaft 202 with a proximal end 202a and a distal end 202b. The cryoablation probe 200 also includes a hand piece 204. The hand piece 204 includes a pistol grip 204a, a finger grip 204b, a pistol trigger 204c, a button 204d, a finger grip barrel 204e, and a housing 204f for a liquid cryogen reservoir. The hand piece 204 also includes a cryotherapy element 206 with a proximal end 206a and a distal end 206b. The proximal end 206a of the cryotherapy element 206 is coupled to or disposed at the distal end 202b of the shaft 202.

The cryoablation probe 200 includes at least one liquid cryogen channel configured to deliver liquid cryogen from the proximal end 202a to the distal end 202b of the shaft 202. In some implementations, the shaft 202 may be substantially rigid. In other implementations, the shaft 202 may be flexible and may change shape in response to manipulation by a user.

The liquid cryogen reservoir within the housing 204f is supplied with liquid cryogen. In some implementations, the cryoablation probe 200 is configured as a single use, disposable device, so the liquid cryogen reservoir is non-refillable. In other implementations, the cryoablation probe 200 is configured as a reusable device, so the liquid cryogen reservoir may be refillable. In some cases, the liquid cryogen reservoir may be a cartridge that can be replaced with other cartridges that supply additional liquid cryogen for further use of the cryoablation probe 200.

The hand piece 204 may further include a flow control valve for the liquid cryogen. The flow control valve may be disposed in fluidic communication with the liquid cryogen reservoir and the liquid cryogen channel in the shaft 202. The pistol trigger 204c and/or the button 204d act as an actuator for the flow control valve. Operation of the pistol trigger 204c and/or the button 204d causes the liquid cryogen to flow from the liquid cryogen reservoir to the cryotherapy element 206 via the liquid cryogen channel. With the liquid cryogen, the cryotherapy element 206 can cryoablate tissue disposed at the distal end 206b of the cryotherapy element 206.

Figure 3:
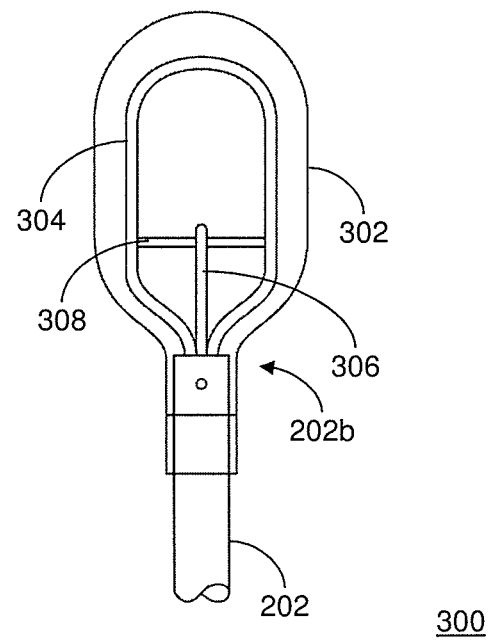
FIG. 3 illustrates an example cryotherapy element for a cryoablation probe.

The cryotherapy element 206 shown in FIG. 2 may have different configurations to achieve effective cryoablation. FIG. 3 illustrates an example cryotherapy element 300 that can be implemented as the cryotherapy element 206 at the distal end 202b of the shaft 202. The cryotherapy element 300 includes an expandable outer structure 302 with a predefined shape. When the liquid cryogen is delivered to the cryotherapy element 300 via the liquid cryogen channel in the shaft 202, the liquid cryogen enters expandable outer structure 302, which expands to the predefined shape through evaporation of the liquid cryogen into a gas. The cryogen in the expandable outer structure 302 allows cryoablation of tissue.

The cryotherapy element 300 also includes an inner structure 304 disposed in the expandable outer structure 302. The expandable outer structure 302 may enclose the inner structure 304 entirely without being attached to the inner structure 304 directly. As shown in FIG. 3, the inner structure 304 is a flat loop that provides a curved, atraumatic shape. The inner structure 304 may be formed of a relatively rigid wire or the like, so that the inner structure 304 can maintain its shape when the cryotherapy element 300 is pressed against a tissue surface. The inner structure 304 presents a low-profile as the cryotherapy element 300 is advanced into and through the nasal cavity and between the nasal turbinate tissues. Yet, due to the flat shape and rigidity of the inner structure 304, the inner structure 304 allows the cryotherapy element 300 to be more easily manipulated within and moved (e.g., pushed) through the nasal cavity. The cryotherapy element 300 does not have to rely on the structure of expandable outer structure 302 to move through the nasal cavity.

As shown in FIG. 3, the cryotherapy element 300 includes a lumen 306 for delivering the liquid cryogen from the shaft 202 into the expandable outer structure 302. The lumen 306 may extend a distance from the distal end 202b of the shaft 202 so that the liquid cryogen is introduced into the expandable outer structure 302 at a more distal location. The cryotherapy element 300 may also include a supporting member 308 (e.g., a bar) that extends across the inner structure 304 to support the lumen 306 transversely within the inner structure 304. In alternative implementations, the cryotherapy element 300 does not include the lumen 306 and the supporting member 308; instead, the inner structure 304 provides sufficient support to allow the liquid cryogen to be introduced directly from the liquid cryogen channel of the shaft 202 and flow through the expandable outer structure 302.

Patients with rhinitis, or other nasal conditions, may experience swelling of mucosal or other tissues in the nasal cavity, further limiting space for a user to operate and maneuver. Moreover, access to certain tissue regions may be limited or impossible. Aspects of the implementations allow a cryoablation probe to be more easily manipulated within and moved through the nasal cavity.

Implementations can ablate tissue in targeted treatment regions in the nasal cavity (e.g., the PNN 108, the APNN) while protecting tissue in other non-treatment regions (e.g., the SPA 112) from unintentional collateral effects. In particular, implementations are configured to prevent cold temperatures associated with cryoablation from causing unintentional collateral effects in non-treatment regions.

In some implementations, a cryoablation probe protects tissue in non-treatment regions from unintentional collateral effects by employing an ultrasound transducer to deliver a focused ultrasound (FUS) beam to the non-treatment regions. The application of FUS to a region of tissue generally results in local temperature increase, primarily within the focal zone of the transducer. Portions of the ultrasound beam may be scattered, absorbed, or reflected by tissues, resulting in the temperature increase. Factors that determine heating with a FUS beam include pulse length, frequency, pulse repetition rate, duty cycle, and intensity (often expressed as $I_{SPTA}$—the spatial-peak temporal average intensity). To provide reference, diagnostic ultrasound imaging typically employs $I_{SPTA} < 1$ W/cm$^2$, and often $I_{SPTA} << 1$ W/cm$^2$. In contrast, FUS may utilize much higher intensities, for instance, approximately 50 W/cm2 to approximately 1000 W/cm$^2$ for applications involving limited heating of tissue. Intensities of greater than 1000 W/cm$^2$ may be utilized for HIFU applications intended to cause tissue destruction.

Accordingly, a FUS transducer may be configured to transmit ultrasound energy to and raise the local temperature of non-treatment regions to protect them from damaging low temperatures induced during cryoablation. The increased temperatures establish a thermal gradient that provides resistance to the ice ball created during cryoablation and helps prevent spreading of cold temperatures from the targeted treatment region to non-treatment regions. FUS may be applied before, during and/or after cryoablation to protect the region.

Figure 4A:
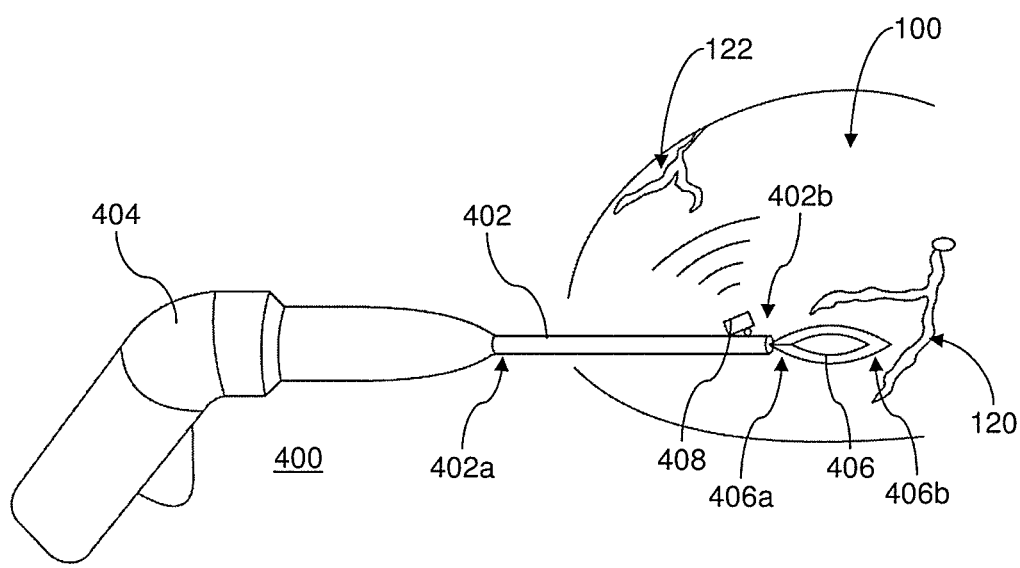
FIG. 4A illustrates an example cryoablation probe including a focused ultrasound (FUS) transducer that applies ultrasound energy to non-treatment regions to protect tissue from effects of cryoablation.

FIG. 4A illustrates an example cryoablation probe 400. Aspects of the cryoablation probe 400 may be similar to the cryoablation probe 200 described above. The cryoablation probe 400 includes a shaft 402, a hand piece 404, and a cryotherapy element 406. The shaft 402 includes a proximal end 402a and a distal end 402b. The cryotherapy element 406 includes a proximal end 406a and a distal end 406b. The proximal end 406a of the cryotherapy element 406 is coupled to or positioned at the distal end 402b of the shaft 402. The hand piece 404 may be operated to deliver liquid cryogen, via the shaft 402, to the cryotherapy element 406 to cryoablate a targeted treatment region positioned at the distal end 406b.

The cryoablation probe 400 also includes a FUS transducer 408 mounted on the shaft 402, proximate to the cryotherapy element 406. As shown in FIG. 4A, the cryotherapy element 406 is positioned in the nasal cavity 100 near a treatment region 120 targeted for cryoablation. Meanwhile, the FUS transducer 408 is configured to deliver ultrasound energy to and generate localized heat in a non-treatment region 122 in the nasal cavity 100. The non-treatment region 122 may be relatively remote from the cryoablation probe 400. Because the ultrasound energy can be delivered across space in a beam, the cryoablation probe 400 does not require direct physical contact with the non-treatment region 122 to protect it from cold temperature effects during cryoablation. This is particularly advantageous when performing ablation in the small, confined space of the nasal cavity.

In some implementations, the FUS transducer 408 may have a fixed focal depth. In other implementations, the FUS transducer 408 may have multiple focal depths that are adjustable by a user to accommodate patient-specific anatomy.

In some implementations, the FUS transducer 408 may be mounted at a fixed angle and a fixed position relative to the rest of the cryoablation probe 400. In other implementations, the angle and/or position of the FUS transducer 408 can be grossly adjusted to redirect the aiming and/or focus of the ultrasound energy. For instance, the FUS transducer 408 may be mounted on a track that allows the FUS transducer 408 to slide relative to the rest of the cryoablation probe 400. Additionally or alternatively, the FUS transducer 408 may be mounted in a manner that allows the FUS transducer 408 to articulate or pivot and scan an arc.

Figure 4B:
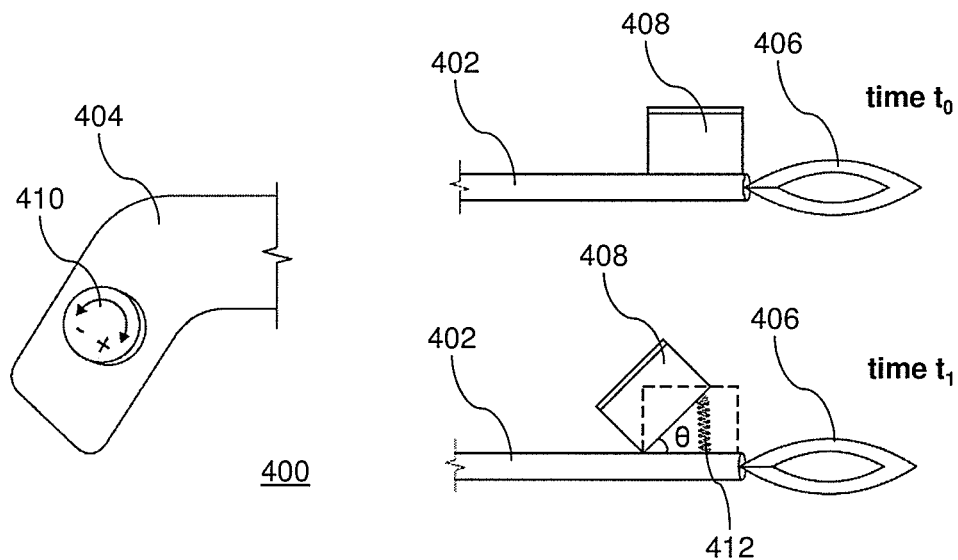
FIG. 4B illustrates an example cryoablation probe that can adjust a direction of ultrasound energy from an FUS transducer.

FIG. 4B, for instance, illustrates an implementation of the cryoablation probe 400 that also includes a dial (or switch) 410 coupled to the hand piece 404. The user can selectively operate the dial 410 to adjust the direction of the ultrasound energy from the FUS transducer 408 and/or to expand the coverage of the FUS transducer 408. In particular, the dial 410 may be coupled to an adjustment mechanism 412 configured to raise or lower an aspect of the FUS transducer 408. The adjustment mechanism 412 adjusts an angle between the FUS transducer 408 and the shaft 402 where the FUS transducer 408 is mounted. As shown in FIG. 4B, the FUS transducer 408 moves from an angle of zero at time $t_0$ to an angle of $\theta_1$ at time $t_1$.

Figure 4C:
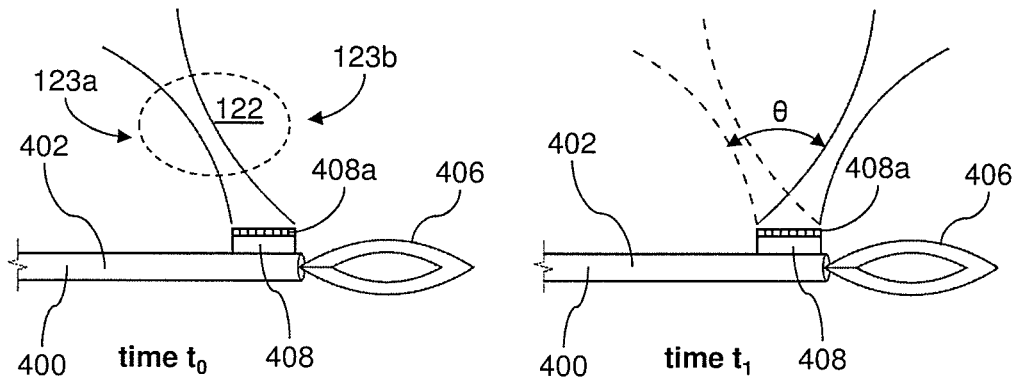
FIG. 4C illustrates another example cryoablation probe that can adjust a direction of ultrasound energy from an FUS transducer.

The position and/or the angle of the FUS transducer 408 can also be more finely adjusted. For instance, the FUS transducer can be pivoted through a smaller angular range than shown in FIG. 4B. In some implementations, fine adjustments may be controlled automatically by software. In some implementations, the direction of the ultrasound energy may be adjusted via electronic/phased steering in the FUS transducer 408. FIG. 4C, for instance, illustrates an implementation of the cryoablation probe 400, where the FUS transducer 408 includes piezoelectric elements 408a. The FUS transducer 408 remains at a fixed position relative to the rest of the cryoablation probe 400. Electronics in the hand piece 404 can adjust the relative phasing of the piezoelectric elements 408a to steer a beam of the ultrasound energy across an anterior boundary 123a and a posterior boundary 123b of the non-treatment region 122. As shown in FIG. 4C, the beam spans an angular variation $\theta_1$ between time $t_0$ to time $t_1$. For purposes of visualization, the span of the angular variation $\theta_1$ has been exaggerated. In an example, the beam of the ultrasound energy is depicted by parabolic shapes as shown. In some implementations, the steering adjustments may be programmed in software. For instance, parameters such as oscillation speed, oscillation angle, and time at each angular position may be provided as input by the user prior to treatment, and the software may control the steering adjustments accordingly. In other implementations, a user may select from a plurality of pre-programmed oscillation profiles.

In some implementations, a cryoablation probe may include a plurality of FUS transducers. This can allow the non-treatment regions to be insonified (i.e., receive ultrasound energy) from different angles and/or with overlapping beams. In some cases, each of the FUS transducers may operate using the same transmit parameters. In other cases, at least one of the FUS transducers may operate using different parameters from another FUS transducer. Implementations that employ a plurality of FUS transducers may enhance remote insonification of certain anatomical regions, thereby improving the ability to protect the non-treatment regions during cryoablation. Because the ultrasound energy can be delivered more effectively across space, the cryoablation probe does not require direct physical contact with the non-treatment regions. This is particularly advantageous when performing ablation in the small, confined space of the nasal cavity.

In some implementations, the FUS transducer may employ continuous wave output to apply energy to the non-treatment regions. In other implementations, the FUS transducer may employ pulsed output to apply energy to the non-treatment regions. In some cases, implementations may employ pulses that range from approximately 0.0001 seconds to 10 seconds long. For instance, pulses may range from approximately 0.001 seconds to approximately 0.01 seconds long. Or alternatively, pulses may range from approximately 5 seconds to approximately 10 seconds long. In some cases, implementations may employ pulse repetition rates ranging from approximately 10 Hz to approximately 10 kHz. For instance, pulse repetition rates may range from approximately 500 Hz to approximately 1 kHz. In some cases, implementations may employ a range of duty cycles based upon the selected pulse length and the selected pulse repetition rate. For instance, the duty cycle may range from approximately 10% to approximately 90%.

In some implementations, the FUS transducer may be configured so the focal depths of the transducer match the tissue depth of the non-treatment regions. For instance, when used in a nasal cavity, the FUS transducer may be configured to apply ultrasound energy at focal depths in a range of approximately 2 mm to approximately 25 mm. Some implementations may employ FUS transducers with a fixed focal depth. Other implementations may employ FUS transducers with adaptive focusing achieved through element-phasing and/or mechanical approaches.

In some implementations, the FUS transducer may employ ultrasound emission frequencies suitable for selected focal depth(s). The ultrasound frequencies employed may affect a number of parameters for operation including, but not limited to, depth of penetration of the ultrasound beam into tissue, size of focal zone, and degree of ultrasound absorption (and thus temperature increase). In some implementations, the FUS transducer transmits using a frequency in the range of approximately 0.1 MHz to approximately 20 MHz. In other implementations, the transmit frequencies may range from approximately 1 MHz to approximately 5 MHz or, in further variations, from approximately 5 MHz to approximately 10 MHz. Some implementations may employ a single fixed ultrasound emission frequency for the FUS transducer. Other implementations may employ a broadband FUS transducer capable of multiple user-selectable ultrasound emission frequencies. Further implementations may allow for several ultrasound emission frequencies to be employed simultaneously by one or more FUS transducers.

Some implementations may utilize focal zone intensities that range from approximately 10 W/cm$^2$ to approximately 1000 W/cm$^2$. In some cases, focal zone intensities may vary between approximately 100 W/cm$^2$ and approximately 500 W/cm$^2$. In some implementations, the transmitted power from the FUS transducer may be fixed. In other implementations, the transmitted power may vary either automatically or under user control. When other ultrasound parameters are held constant, temperature increases in tissue due to the operation of FUS transducers are directly proportional to the transmit intensity. In some implementations, peak temperature increases in the non-treatment region may range from approximately 1° C. to approximately 5° C. In other implementations, peak temperature increases may exceed approximately 5° C., but for limited periods of time exposure that do not lead to significant thermal effects on the tissue.

Rather than employing active temperature monitoring, temperature increases in the non-treatment regions may be estimated prior to treatment based on intensity and other parameters employed by the FUS transducer. Because tissue properties may not be known with a high degree of precision prior to initiating a treatment, a safety margin may be employed when determining the most suitable ultrasound intensity which will not elevate temperatures beyond a level that is well-tolerated by the non-treatment regions.

Figure 5:
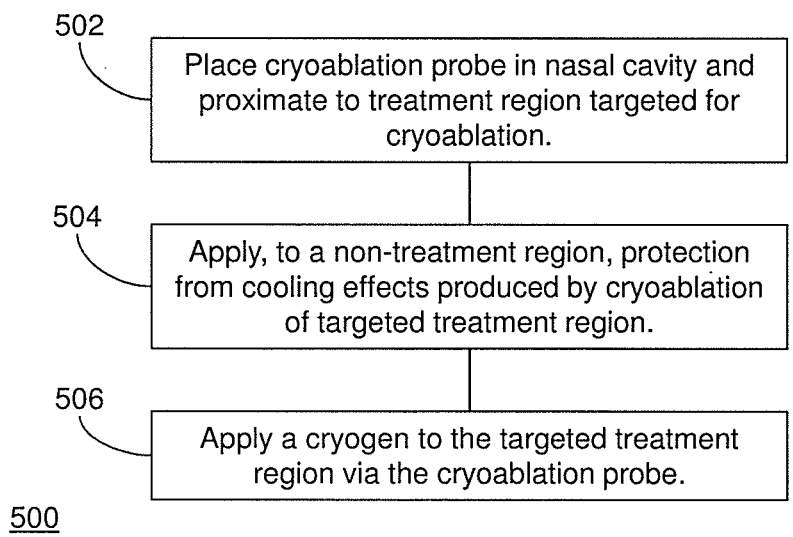
FIG. 5 illustrates an example process for treating a nasal condition.

FIG. 5 illustrates an example process 500 for treating a nasal condition, such as rhinitis. Act 502 involves placing a cryoablation probe in a nasal cavity and near the treatment region targeted for cryoablation. Act 504 involves applying, to another non-treatment region, protection from cooling effects produced by the cryoablation of the targeted treatment region, wherein the cryoablation probe is remote from the targeted treatment region and transmits the protection to the other region across space. Act 506 involves applying a cryogen to the targeted treatment region via the cryoablation probe.

In some implementations, the process 500 may include additional acts. For instance, an additional act may involve the removal of the cryoablation probe from the treatment area. Or a further act may involve applying additional protection following the application of the cryogen to the targeted treatment region.

The acts in process 500 may be performed in any order. Optionally, an act in process 500 may be repeated. For instance, the following order of acts may be performed: (i) according to act 502, the cryoablation probe is placed in a nasal cavity and proximate to the region targeted for cryoablation; (ii) according to act 506, a cryogen is applied to the targeted treatment region via the cryoablation probe; (iii) according to act 504, protection is applied to another region from cooling effects produced by the cryoablation of the targeted treatment region; and (iv) according to act 506, a cryogen is applied to the targeted treatment region via the cryoablation probe.

In some implementations, act 504 may be applied one or more times prior to the cryoablation in act 506. Additionally or alternatively, act 504 may be applied actively one or more times during the cryoablation in act 506. Additionally or alternatively, act 504 may be applied one or more times after the cryoablation in act 506. Furthermore, act 504 may be applied for any duration(s).

In some implementations, act 504 is achieved by applying heat to increase temperature in the non-treatment region. In particular, the heat may be generated by ultrasound energy provided by an FUS transducer, which may be integrated into or otherwise adapted for use with the cryoablation probe. The ultrasound energy is absorbed or reflected by tissue in the non-treatment region.

Other implementations may employ mechanisms for actively monitoring temperatures in treatment and/or non-treatment regions during treatment. Temperatures in regions that are located near the cryoablation probe can be measured using a temperature sensor (e.g., one or more thermocouple sensors, thermistor sensors, and/or infrared sensors). Temperatures in regions located more remotely from the cryoablation probe, i.e., the non-treatment regions, can be measured using other approaches. One approach, for instance, may employ thermal strain imaging, an ultrasound-based technique that uses real or apparent shifts in the speed of sound of tissue caused by temperature changes in the tissue to estimate the magnitude of the temperature changes.

Figure 6A:
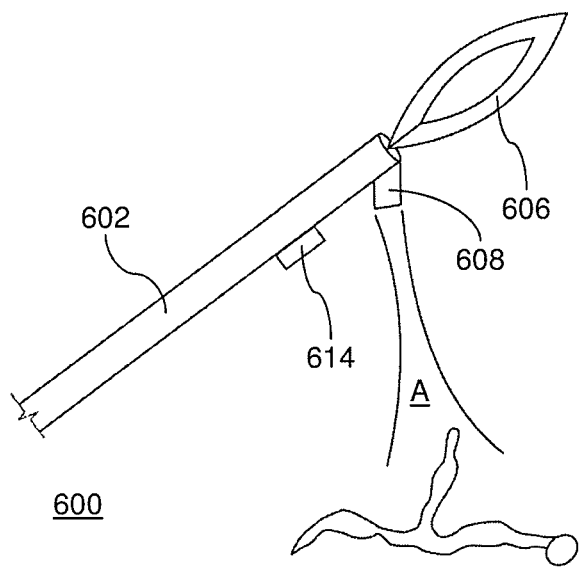
FIG. 6A illustrates an example cryoablation probe that includes a FUS transducer and an imaging ultrasound transducer, where the FUS transducer transmits ultrasound energy to protect a non-treatment region from cold temperatures resulting from cryoablation.

FIG. 6A illustrates an example cryoablation probe 600. Aspects of the cryoablation probe 600 may be similar to the cryoablation probe 200 described above. As shown, the cryoablation probe 600 includes a shaft 602 and a cryotherapy element 606. The cryotherapy element 606 is coupled to the shaft 602. The cryoablation probe 600 is operated to deliver liquid cryogen, via the shaft 602, to the cryotherapy element 606 to cryoablate a targeted treatment region positioned at the distal end 606b of the cryotherapy element 606.

Figure 6B:
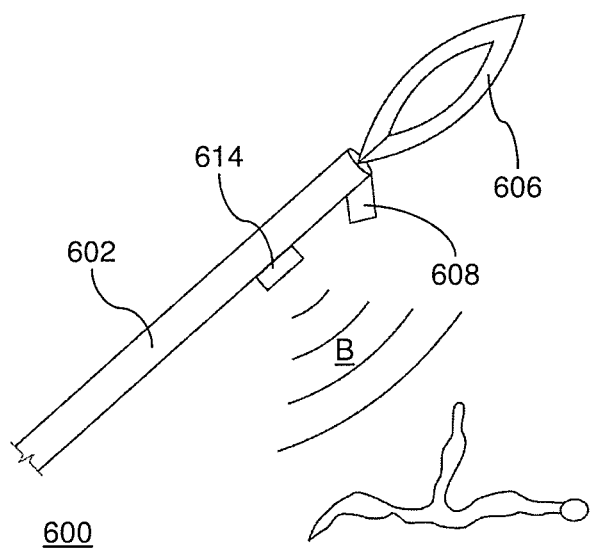
FIG. 6B illustrates the example cryoablation probe of FIG. 6A, where the imaging ultrasound transducer is employed for thermal strain imaging.

The cryoablation probe 600 also includes a FUS transducer 608 and an imaging ultrasound transducer 614 coupled to or otherwise disposed on the shaft 602. As shown in FIG. 6A, the FUS transducer 608 can transmit ultrasound energy A to protect a non-treatment region from cold temperatures resulting from cryoablation. Meanwhile, FIG. 6B shows that the imaging ultrasound transducer 614 can transmit ultrasound energy B to the same non-treatment region. The imaging ultrasound transducer 614 can capture tissue echoes for thermal strain imaging. Imaging ultrasound transducer 614, however, employs lower intensity than the FUS transducer 608. Accordingly, implementations can employ ultrasound transducers that provide FUS to treat tissue and imaging and/or temperature information to monitor the treatment.

Figure 7:
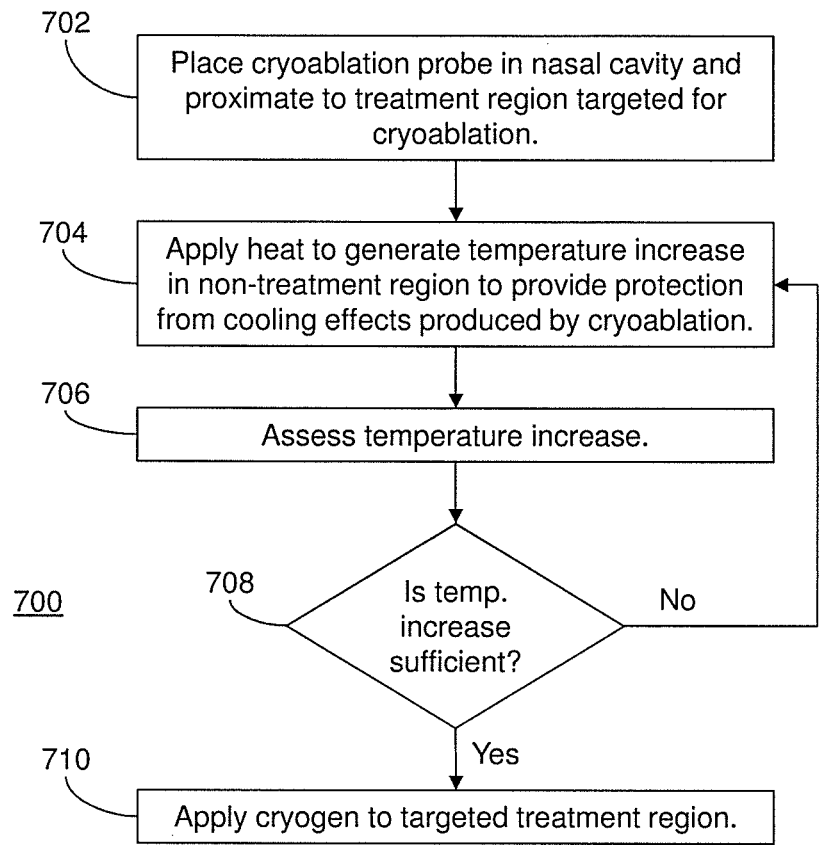
FIG. 7 illustrates another example process for treating a nasal condition.

In some implementations, cryoablation does not begin until the thermal strain imaging indicates that the temperature in the non-treatment region has increased to a level that is sufficient to protect the non-treatment region from cold temperatures generated by cryoablation. If the thermal strain imaging indicates that the temperature of the non-treatment region is lower than desired, the FUS transducer 608 can transmit additional ultrasound energy to increase the temperature further. Alternatively or additionally, another temperature monitoring technique such as infrared imaging may be used to ensure that the temperature in the non-treatment region has increased to a level that is sufficient to protect the non-treatment region from cold temperatures generated by cryoablation. Correspondingly, FIG. 7 illustrates an example process 700 for treating a nasal condition, such as rhinitis. Act 702 involves placing a cryoablation probe in a nasal cavity and near the region targeted for cryoablation. Act 704 involves applying heat to generate a temperature increase in a non-treatment region to provide protection from cooling effects produced by the cryoablation of the targeted treatment region. An FUS transducer, for instance, may be employed to generate the temperature increase in act 704. Act 706 involves assessing the temperature increase generated in act 704. Thermal strain imaging with an imaging ultrasound transducer or magnetic resonance (MR) thermography may be employed to assess the temperature increase in act 706. Act 708 involves determining if the temperature increase assessed in act 706 is sufficient to protect the non-treatment region during cryoablation of the targeted treatment region. If the temperature increase is sufficient, the process 700 continues to act 710, which involves applying a cryogen to treat the targeted treatment region. If the temperature increase is insufficient, the process returns to act 704 so that additional heat can be generated to provide a further temperature increase in the non-treatment region. The process 700 can then proceed again to acts 706 and 708 to evaluate the temperature of the non-treatment region and determine if more heat should be generated in the non-treatment region. The acts 704, 706, and 708 can be repeated until the temperature increase is found to be sufficient to protect the non-treatment region.

Figure 8:
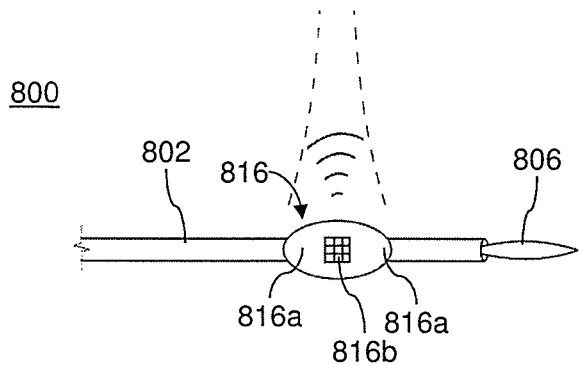
FIG. 8 illustrates a view of an example cryoablation probe that includes a combined transducer device with hyperthermia-inducing transducer element(s) and an imaging transducer element.

FIG. 8 illustrates an example cryoablation probe 800. Aspects of the cryoablation probe 800 may be similar to the cryoablation probe 200 described above. As shown, the cryoablation probe 800 includes a shaft 802 and a cryotherapy element 806. The cryotherapy element 806 is coupled to the shaft 802. The cryoablation probe 800 is operated to deliver liquid cryogen, via the shaft 802, to the cryotherapy element 806 to cryoablate a targeted treatment region positioned at the cryotherapy element 806.

The cryoablation probe 800 includes a combined transducer device 816 coupled to or otherwise disposed on the shaft 802. The combined transducer device 816 includes a hyperthermia-inducing transducer element(s) 816a and an imaging transducer element 816b. The combined transducer device 816 may have a curved housing. The imaging transducer element 816b is positioned centrally on the curved housing, while the hyperthermia-inducing transducer element(s) 816a are positioned at the lateral edges of the curved housing 816c. The position of the hyperthermia-inducing transducer element(s) 816a assists with focusing of the ultrasound energy from the hyperthermia-inducing transducer element(s) 816a.

FIG. 8 illustrates an imaging acoustic field from the imaging transducer element 816b with solid lines and the acoustic field from the hyperthermia-inducing transducer element(s) 816a with dashed lines. The acoustic field lines are shown for illustrative purposes only and are not necessarily representative of absolute or relative field shapes during use of the combined transducer device 816. Although both acoustic fields are shown in the figure, implementations might not simultaneously employ both transducer elements 816a, b to limit any interference from beam interactions that may reduce the accuracy of diagnostic measures.

In some implementations, a single transducer may be employed to apply hyperthermic ultrasound energy to protect tissue and to monitor the response with thermal strain imaging. In other implementations, more than two transducers may be used.

Acoustic coupling may be employed to enhance the emission of ultrasound energy from an FUS transducer to a targeted treatment region. For instance, a region containing a gas (such as air) may result in a strong reflection of ultrasound energy at the edge of the region, and if such a region exists between the FUS transducer and the non-treatment region, little to no ultrasound energy may reach the non-treatment region. Accordingly, a mechanism to provide acoustic coupling between the FUS transducer and non-treatment region may be advantageous when performing procedures in the nasal cavity, a region where air is abundant.

Figure 9:
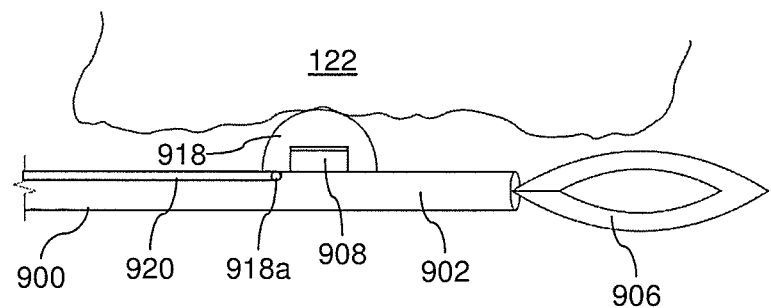
FIG. 9 illustrates an example cryoablation probe that includes a coupling balloon to enhance acoustic coupling and delivery of ultrasound energy from a FUS transducer to a non-treatment region.

FIG. 9 illustrates an example cryoablation probe 900. Aspects of the cryoablation probe 900 may be similar to the cryoablation probe 200 described above. As shown, the cryoablation probe 900 includes a shaft 902 and a cryotherapy element 906. The cryotherapy element 906 is coupled to the shaft 902. The cryoablation probe 900 is operated to deliver liquid cryogen, via the shaft 902, to the cryotherapy element 906 to cryoablate a targeted treatment region positioned at the cryotherapy element 906.

The cryoablation probe 900 includes an FUS transducer 908 coupled to the shaft 902 to deliver ultrasound energy to the non-treatment region 122 as described above. Additionally, the cryoablation probe 900 includes a coupling balloon 918 that encloses the FUS transducer 908. The coupling balloon 918 may be formed from a thin but robust material, such as 1 mil to 5 mil polyethylene, where the coupling balloon 918 can maintain structural integrity under normal operating conditions but is substantially acoustically invisible to the ultrasound signal. In some implementations, the coupling balloon 918 may be initially collapsed or deflated to provide the coupling balloon 918 with a low profile for easier manipulation and navigation of the cryoablation probe 900 in the confined space of the nasal cavity. Once the cryoablation probe 900 is in the desired position for cryoablation, the coupling balloon 918 may be inflated until the coupling balloon 918 makes contact with the non-treatment region 122. This contact provides an acoustic coupling between the FUS transducer 908 and the non-treatment region 122 to improve the delivery of the ultrasound energy to the non-treatment region 122 and increase the temperature of the non-treatment region 122 as described above. The coupling balloon 918 can be inflated by pumping a fluid (e.g., degassed, dionized water) or gel through an opening 918a of the coupling balloon 918. The fluid or gel may be stored in a compartment, for instance, in the hand piece, and a conduit 920 integrated with or coupled to the shaft 902 can direct the fluid or gel to the opening 918a. The fluid or gel has acoustic properties that provide an effective acoustic coupling between the FUS transducer 908 and the non-treatment region 122.

Figure 10:
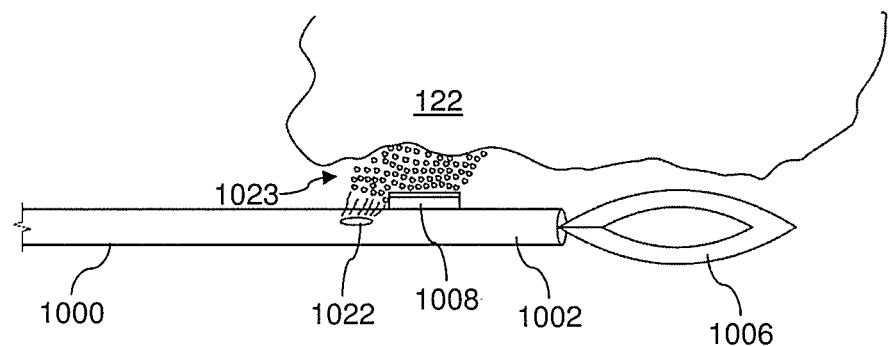
FIG. 10 illustrates an example cryoablation probe that aspirates a mist to enhance acoustic coupling and delivery of ultrasound energy from a FUS transducer to a non-treatment region.

FIG. 10 illustrates an example cryoablation probe 1000. Aspects of the cryoablation probe 1000 may be similar to the cryoablation probe 200 described above. As shown, the cryoablation probe 1000 includes a shaft 1002 and a cryotherapy element 1006. The cryoablation probe 1000 is operated to deliver liquid cryogen, via the shaft 1002, to the cryotherapy element 1006 to cryoablate a targeted treatment region positioned at the cryotherapy element 1006.

The cryoablation probe 1000 includes an FUS transducer 1008 coupled to the shaft 1002 to deliver ultrasound energy to the non-treatment region 122 as described above. The shaft 1002 includes an aspiration vent 1022 that can release a fine, dense mist 1023 into the vicinity of the FUS transducer 1008. Over short distances the mist 1023 can provide an acoustic coupling that enables sufficient ultrasound energy from the FUS transducer 1008 to reach the non-treatment region 122 and increase the temperature of the non-treatment region 122 as described above. In contrast to other approaches, the use of mist to enhance acoustic coupling allows the cryoablation probe 1000 to have a smaller and narrower form factor, which allows easier manipulation and navigation in the confined space of a nasal cavity.

Application of a cryoablation probe in a patient may depend on the patient's particular anatomy. As such, it may not be possible to know how the cryoablation probe should be positioned and oriented to cryoablate targeted tissue while also implementing any of the approaches above to protect non-treatment regions. For instance, proper orientation of the cryoablation probe allows a FUS transducer to effectively transmit ultrasound energy in the direction of the non-treatment region as described above. Positioning and orienting the cryoablation probe in specific locations of the nasal cavity, e.g., near the posterior aspect of the middle turbinate, to cryoablate targeted tissue is further complicated by simultaneously identifying non-treatment regions as well as positioning and orienting the FUS transducer to protect the non-treatment regions.

Example implementations may involve: (i) positioning a cryoablation probe in a location where cryoablation can be applied to a targeted treatment region; (ii) while keeping the instrument location unchanged, identifying an anatomical indicator that reveals the location of a non-treatment region that should be protected from cold temperature effects caused by the cryoablation; (iii) adjusting the position of a protection mechanism, e.g., a FUS transducer, to provide protection accurately to the identified non-treatment region; (iv) operating the protection mechanism to protect the identified non-treatment region from the possible cold temperature effects; and (v) applying the cryoablation to the targeted treatment region. In some implementations, the protection mechanism can be operated during and/or after the cryoablation is applied to the treatment region. Identifying the anatomical indicator may involve using an ultrasound signal from an ultrasound transducer, which may produce a standard echo A-mode or B-mode signal, a Doppler signal, or some combination thereof.

For instance, referring to FIGS. 6A-B, the cryotherapy element 606 of the cryoablation probe 600 can remain positioned near the PNN, while the imaging ultrasound transducer 614 can scan a range of angles in search of the SPA. The imaging ultrasound transducer 614 can scan the range of angles by using approaches similar to those disclosed for the FUS transducer 408 in FIGS. 4A-C. The scanned regions reflect the ultrasound signals emitted by the imaging ultrasound transducer 614. The imaging ultrasound transducer 614 receives the reflected ultrasound signals, which can then be processed (e.g., by a controller) for characteristics that indicate the location of the SPA. The reflected ultrasound signals can be processed automatically by software with signal processing algorithms that use machine-learning, artificial intelligence, etc. For example, for A-mode or B-mode imaging, the software may search for hypoechoic regions commonly associated with the presence of blood vessels in the scan plane. As another example, Doppler or power Doppler signals may be examined by algorithms searching for phase shifts or power levels indicative of blood flow in the scanned regions. Once the SPA is located, the FUS transducer 608 can be aimed appropriately to emit ultrasound energy to the SPA region and heat the SPA region to temperatures that can resist cold temperatures generated by cryoablation of the PNN. Once sufficient heating and temperature increase has been achieved, the cryoablation probe 600 can begin cryoablation of the PNN. Thus, implementations can protect non-treatment regions without requiring knowledge of the exact location of the non-treatment region at the beginning of the treatment. Although the cryoablation probe 600 may be employed with separate imaging and FUS transducers, other implementations may employ a cryoablation probe with a combined transducer, e.g., combined transducer device 816 of the cryoablation probe 800, for both imaging and FUS signals.

Certain anatomies may include multiple non-treatment regions (i.e., multiple locations of non-treatment regions) that are near the treatment regions targeted for cryoablation. Moreover, in some scenarios, the cryoablation may affect these multiple non-treatment regions at different times due to tissue anatomy and/or physiology. Advantageously, in some implementations, a single FUS transducer can protect the multiple non-treatment regions. Such implementations limit the complexity of and reduce the size of the cryoablation probe.

Figure 11A:
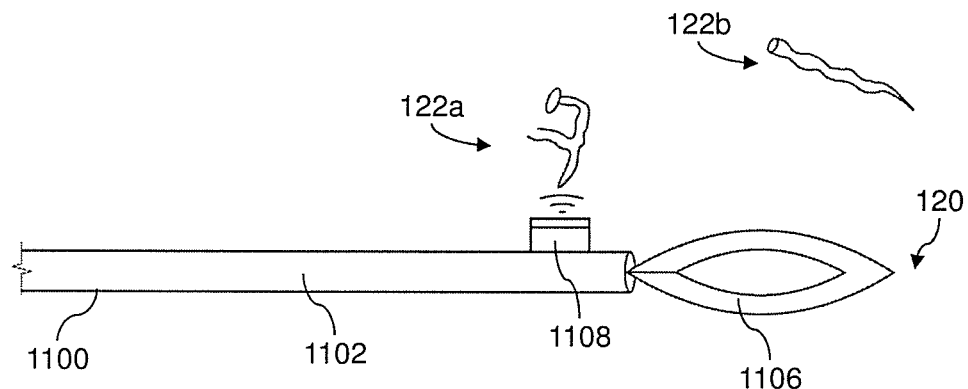
FIG. 11A illustrates an example cryoablation probe that includes a FUS transducer configured to deliver ultrasound energy to multiple non-treatment regions.
Figure 11B:
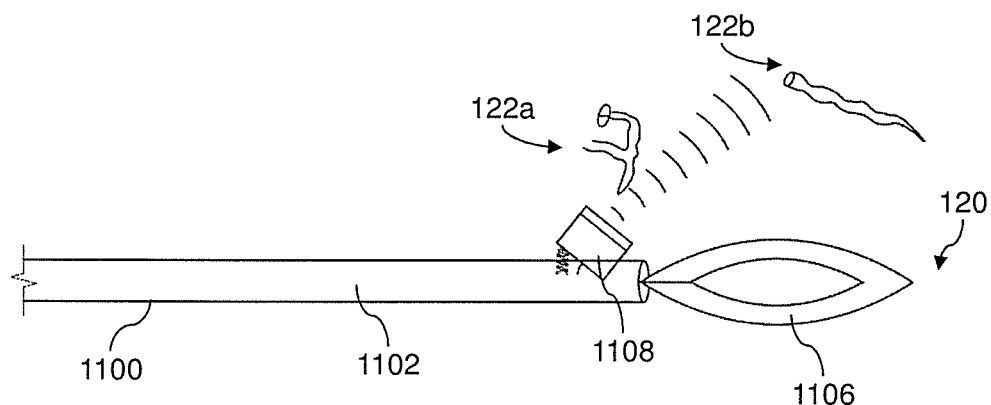
FIG. 11B further illustrates the example cryoablation probe of FIG. 11A.

FIGS. 11A-B illustrate an example cryoablation probe 1100. Aspects of the cryoablation probe 1100 may be similar to the cryoablation probe 200 described above. As shown, the cryoablation probe 1100 includes a shaft 1102 and a cryotherapy element 1106. The cryoablation probe 1100 is operated to deliver liquid cryogen, via the shaft 1102, to the cryotherapy element 1106 to cryoablate the targeted treatment region 120 positioned near the cryotherapy element 1106.

As shown in FIG. 11A, the targeted treatment region 120 is disposed near a first non-treatment region 122a and a second non-treatment region 122b, both of which are preferably protected from cold temperature effects caused by the cryoablation. The second non-treatment region 122b is more distant from the targeted treatment region 120 than the first non-treatment region 122a. Assuming reasonable tissue homogeneity, cold temperatures from cryoablation at the targeted treatment region will reach the first non-treatment region 122a before the second non-treatment region 122b.

The cryoablation probe 1100 also includes an FUS transducer 1108 coupled to the shaft 1102 to deliver to deliver ultrasound energy as described above. The FUS transducer 1108 can be first employed to emit ultrasound energy to the first non-treatment region 122a to initiate a temperature increase. Cryoablation of the targeted treatment region 120 may begin when desired temperature increase at the first non-treatment region 122a is achieved. The position and/or orientation of the FUS transducer 1108 can then be adjusted as shown in FIG. 11B to emit ultrasound energy to the second non-treatment region 122b to initiate a temperature increase. The FUS transducer 1108 can be adjusted to heat the non-treatment region 112b before cryoablation of the targeted treatment region 120 begins.

Figure 12:
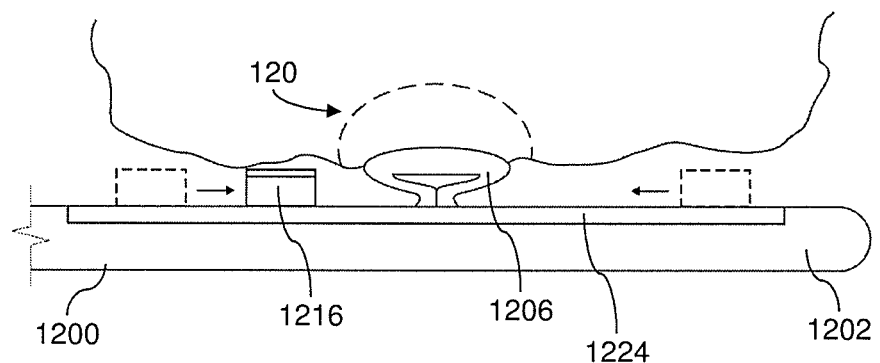
FIG. 12 illustrates an example cryoablation probe that can actively sense a risk of cold temperature effects on a non-treatment region and can dynamically apply protection to the non-treatment region.

Some implementations can actively sense when there is risk of cold temperature effects on a non-treatment region and can dynamically apply protection to the non-treatment region. FIG. 12 illustrates an example cryoablation probe 1200 with a shaft 1202 and a cryogen-delivery element 1206. The cryogen-delivery element 1206 is disposed at an intermediate position on the shaft 1202. The cryoablation probe 1200 is operated to deliver liquid cryogen, via the shaft 1202, to the cryogen-delivery element 1206 to cryoablate the targeted treatment region 120 positioned near the cryogen-delivery element 1206.

The cryoablation probe 1200 includes a combined transducer device 1216 with a hyperthermia-inducing transducer element and an imaging transducer element. The combined transducer device 1216 is movably mounted on a track 1224 that allows the combined transducer device 1216 to move laterally along the shaft 1202. In an imaging mode, the combined transducer device 1216 can be employed to scan regions in the vicinity of the targeted treatment region 120. In this mode, the combined transducer device 1216 can assess temperatures and/or temperature changes by using image processing techniques, such as thermal strain imaging, or by detecting power density/brightness changes caused by an advancing ice ball, a change in density, a change in sound speed, or an alteration of other known temperature-dependent tissue properties. Temperature monitoring (e.g., by a controller) may occur constantly during and following the application of the cryogen to the targeted treatment region 120. If the temperature monitoring identifies dangerously low temperatures approaching a non-treatment region that should be protected from significant thermal effects, the combined transducer device 1216 may switch to a hyperthermia-inducing mode and apply ultrasound energy to increase the temperature of this region to resist the low temperatures.

Although the cryoablation probe 1200 may be employed with a combined transducer, other implementations may employ separate imaging and FUS transducers. Moreover, multiple imaging ultrasound transducers and/or multiple FUS transducers may be employed.

Figure 13:
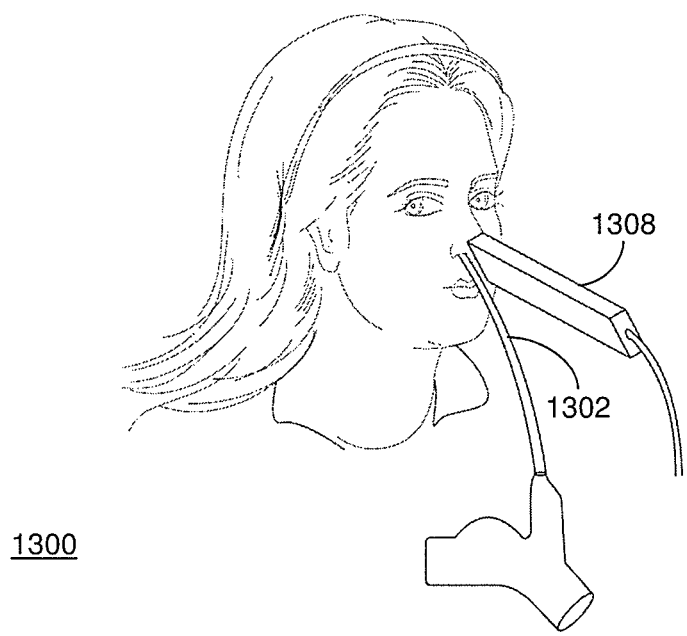
FIG. 13 illustrates yet another example process for treating a nasal condition.

In some instances, it may be advantageous to employ a cryoablation device separately from the protection mechanisms described above. In particular, in the confined space of the nasal cavity, it may be advantageous to minimize the size of a cryoablation probe by separating it from the transducer hardware described above. FIG. 13 illustrates an example process 1300 for treating a nasal condition. A FUS transducer 1308 may be applied to a patient (e.g., exterior side of the nose, side of the face (e.g., the cheek), the roof of the mouth just medial to the molars, etc.) to increase the temperature of a non-treatment region that should be protected from the effects of cryoablation. Simultaneously, a separate cryoablation probe 1302 may be inserted in the nasal cavity via a nostril and positioned near the PNN, APNN, or other targeted treatment region.

In some implementations, the FUS transducer 1308 is configured to fit inside the nasal cavity alongside the cryoablation probe 1302 and direct ultrasound energy toward the posterior inferior meatus or inferior portion of the Sphenoethmoid recess. In other implementations, the FUS transducer 1308 is configured to enter the mouth and apply ultrasound energy to the soft palate, the hard palate, and/or the greater palatine foramen, while the cryoablation probe 1302 is configured to enter the nasal cavity and treat tissues proximate to the inferior, middle, or superior turbinates.

In some implementations, the FUS transducer 1308 may apply ultrasound energy directly to the non-treatment region. In alternative implementations, the transducer may apply ultrasound energy to a different region and allow thermal conduction and/or the flow of blood to carry the heat to desired non-treatment regions. These implementations may be particularly advantageous given the limited acoustic windows (absent bone or air-filled sinuses which reflect incident ultrasound signal) into the nasal cavity for transducers applied externally. The vein or artery selected for delivering heat may extend directly between the region receiving the ultrasound energy and the non-treatment region. Alternatively, the vein or artery selected for hyperthermia may be upstream or downstream from a vessel that passes near the non-treatment region. For instance, the sphenopalatine and palatine veins empty into the pterygoid plexus (a collection of veins between the temporalis and lateral pterygoid muscle), and blood that changes temperature within these veins can affect muscles and tissues proximate to this plexus or downstream from the plexus.

Figure 14:
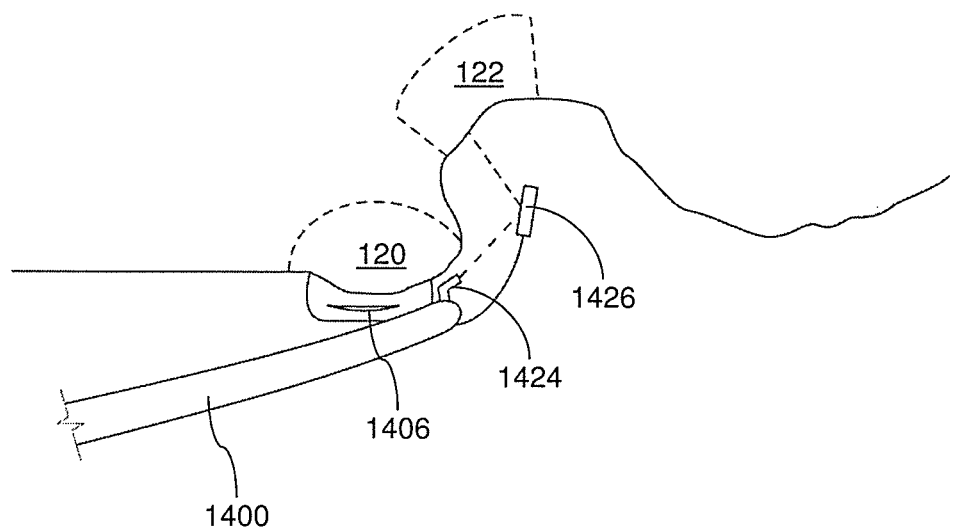
FIG. 14 illustrates an alternative implementation that employs laser energy to increase tissue temperatures.

Although the examples above may employ a transducer to apply ultrasound energy to heat non-treatment regions, alternative implementations may employ non-ultrasound mechanisms. For instance, FIG. 14 illustrates an example implementation that employs laser energy to increase tissue temperatures. Laser energy is attenuated very quickly by soft tissues, and penetration depth is generally described as being on the order of millimeters. As shown in FIG. 14, a cryoablation probe 1400 includes a cryoablative element 1406 positioned at a targeted treatment region 120. The cryoablation probe 1400 also includes a laser source 1424 and a reflective element 1426, such as a mirror. The reflective element 1426 extends from the distal end of the cryoablation probe 1400 and is configured to direct laser energy emitted by the laser source 1424 to non-treatment region 122. The laser energy may be applied prior to, during, or following cryoablation to induce a temperature increase in the non-treatment region 122 and protect the non-treatment region 122 from the effects of the cryoablation.

Aspects of the example implementations above may be applied in other applications, where non-treatment regions are not susceptible to unintentional collateral effects during cryoablation procedures. For instance, bone tissue is known to have tissue properties that allow for rapid induction of hyperthermia when exposed to focused ultrasound. It is also known that unintended cooling of certain bony tissues during cryoablation may lead to patient discomfort, even if this cooling is not of the magnitude required to cause significant thermal effects on the tissue. During cryoablation performed within the nasal cavity, it is possible that certain bony tissues, such as the perpendicular plate of the palatine bone, may be exposed to cold temperatures in a way that manifests as patient discomfort with a sensation similar to that known as the "ice cream headache." Using an ultrasound transducer (or other mechanism) to apply heating to this bone before, during, or following cryotherapy may help limit temperature changes in the bone and may improve patient comfort. The discomfort that manifests may be a latent-onset pain that has been hypothesized to originate from temperature changes induced in vessels or circulating blood traveling within vessels. In some cases this pain may be caused by blood within the vessels carrying abnormal temperatures into different regions away from the targeted treatment region, for example by conveying abnormally cold temperatures into the vicinity of nerve tissues that have not been adequately anesthetized. In some cases this pain may be caused by a cascade of reactions to the initial temperature change, for example vasoconstriction/dilation and the downstream effects this and related physiological changes may impose. Aspects of the present disclosure may be adapted to prevent and/or compensate for these types of reactions to a treatment. In general, implementations may be effective for reducing or eliminating pain or discomfort if heating is applied at any point between the anatomical location where blood temperature is altered and the anatomical location where this altered blood temperature stimulates a noxious response.

In implementations, a focused ultrasound transducer is adapted to apply hyperthermia energy in the tissue region in and/or around a vein or artery, for example the palatine or facial veins or sphenopalatine artery, during a cryoablation procedure involving the PNN, sphenopalatine ganglion, or related nerve target. The transducer is adapted to raise temperatures in targeted tissues by approximately 1° C. to approximately 6° C. These elevated temperatures warm blood in the vessel and this warmed blood will travel away from the hyperthermia application site as part of normal blood flow. This induction of elevated blood temperatures will offset or partially offset any blood temperature decreases caused by application of a cryogen to nearby tissues.

In implementations, a FUS transducer is integrated into an ablation probe and adapted to direct energy to the inferior portion of the nasal cavity once the ablation probe has been inserted into the nose. In implementations, the transducer and ablation probe are separate devices and a method of use includes utilizing a FUS transducer adapted to enter the mouth and direct energy to the soft palate, the hard palate, and/or the greater palatine foramen in conjunction with an ablation probe adapted to enter the nasal cavity and treat tissues proximate to the inferior, middle, or superior turbinates. The FUS transducer may be utilized to elevate vessel and/or tissue temperatures prior to, during, or following ablation procedures, or during some combination of these time periods.

In some implementations, the targeted treatment region is located within a posterior aspect of a middle turbinate and the non-treatment region includes a tarus. In other implementations, the targeted treatment region includes a lateral wall of the nasal cavity and the non-treatment region includes a sinus ostia. In further limitations, the targeted treatment region includes a posterior nasal nerve and the non-treatment region includes a sphenopalatine foramen at least approximately 0.2 cm away from the target treatment site.

In addition to or alternatively to the FUS and laser energy described above, implementations may be configured to alter or prevent the alteration of blood temperatures using high thermal capacity tools placed in the vicinity of a blood vessel or target nerves. In implementations, an ablation probe is inserted into the nasal cavity and positioned proximate to a target tissue. Prior to initiating treatment, a hot (or cold, depending on the ablation modality utilized) thermal device is placed in the subject's mouth at a location proximate to the soft palate, hard palate, or greater palatine foramen. The mouth-based device provides local protection against unwanted tissue temperature changes.

In implementations, the thermal device is adapted to take the shape of a lollipop. The core of the lollipop apparatus may contain a high heat capacity or phase-change material to ensure that its exterior can maintain a consistent warm temperature (e.g., approximately 37° C. to approximately 45° C.) for a prolonged period of time (e.g., approximately 5 minutes to 30 minutes) without the requirement of being excessively hot (e.g., greater than approximately 50° C.) at the initial time of placement. In implementations, the inner phase-change material core of the lollipop apparatus is covered by a hardened sugar material, a plastic material, or a hybrid material that allows for adequate heat conduction from the core to the surface but also is considered suitable to be held in a subject's mouth for a period of time up to 30 minutes.

Implementations may further be configured to alter or prevent the alteration of blood temperatures by injecting a fluid warmed above a patient's body temperature into a blood vessel, foramen, or other space. For example, warmed saline may be injected into the SPA, SPV, or palatine canal.

Although the above disclosed implementations have primarily been discussed in the context of cryoablation, aspects of the implementations may be used with other ablative or non-ablative techniques. For instance, although ablation may be achieved via a cryotherapy element, alternative implementations can apply other cooling techniques to modify tissue(s). Moreover, aspects of the implementations may be applied to non-nasal treatments. Aspects of the implementations may be applied as a standalone system or method, or as part of an integrated medical treatment system. It shall be understood that different aspects of the implementations can be employed individually, collectively, or in combination with each other.

By the term "approximately" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It should be understood from the foregoing that, while particular implementations have been illustrated and described, various modifications can be made thereto and are contemplated herein. It is also not intended that the disclosure be limited by the specific examples provided within the specification. Furthermore, it shall be understood that all aspects of the disclosure are not limited to the specific depictions, configurations, or relative proportions set forth herein which depend upon a variety of conditions and variables. Various modifications in form and detail of the implementations of the disclosure will be apparent to a person skilled in the art. It is therefore contemplated that the disclosure shall also cover any such modifications, variations, and equivalents.

What is claimed is:

1. A system for treating a nasal condition, the system comprising:
    a probe including a shaft and a cryotherapy element coupled to the shaft, wherein the probe is configured to be advanced into a nasal cavity and to cryoablate treatment tissue including at least one nasal nerve at a target treatment site with the cryotherapy element; and
    an ultrasound transducer assembly configured to transmit a focused ultrasound beam to non-treatment tissue at a target heating site to increase a temperature of the non-treatment tissue and to protect the non-treatment tissue from effects of cold temperature produced during cryoablation of the treatment tissue.

2. The system of claim 1, wherein the cryotherapy element and the ultrasound transducer assembly are configured to cryoablate the treatment tissue at the target treatment site and transmit the focused ultrasound beam simultaneously.

3. The system of claim 1, wherein the ultrasound transducer assembly is configured to initiate transmitting the focused ultrasound beam prior to the cryoablation of the treatment tissue at the target treatment site.

4. The system of claim 1, wherein the ultrasound transducer assembly is coupled to the shaft.

5. The system of claim 4, wherein the ultrasound transducer assembly is configured to transmit the focused ultrasound beam by emitting the focused ultrasound beam from the ultrasound transducer assembly at an angle relative to the shaft.

6. The system of claim 5, wherein the ultrasound transducer assembly is configured so that the angle of the focused ultrasound beam is adjustable from a first angle wherein the focused ultrasound beam is directed in a first direction to a second angle wherein the focused ultrasound beam is directed in a second direction different than the first direction.

7. The system of claim 6, wherein the ultrasound transducer assembly is configured so that the angle of the focused ultrasound beam is changed by articulating the angle of the ultrasound transducer assembly relative to the shaft.

8. The system of claim 6, wherein the ultrasound transducer assembly is configured so that the angle of the focused ultrasound beam is changed with phased steering.

9. The system of claim 6, wherein the ultrasound transducer assembly is configured so that while transmitting the focused ultrasound beam to the target heating site, the angle of the focused ultrasound beam relative to the shaft is changeable to transmit the focused ultrasound beam to multiple locations of the target heating site.

10. The system of claim 3, wherein the ultrasound transducer assembly is slidably coupled to the shaft so that a position of the ultrasound transducer assembly along the shaft is changeable from a first position wherein the focused ultrasound beam is not directed to the target heating site to a second position wherein the focused ultrasound beam is directed to the target heating site.

11. The system of claim 3, wherein the ultrasound transducer assembly is slidably coupled to the shaft so while transmitting the focused ultrasound beam to the target heating site a position of the ultrasound transducer assembly along the shaft is changeable to transmit the focused ultrasound beam to multiple locations of the target heating site.

12. The system of claim 4, wherein the ultrasound transducer assembly is configured to transmit the focused ultrasound beam to identified target heating sites based upon a tissue temperature around the target treatment site while cryogenically cooling the target treatment site.

13. The system of claim 12, further comprising a second ultrasound transducer assembly coupled to the shaft and configured to detect the tissue temperature.

14. The system of claim 13, wherein the second ultrasound transducer assembly is configured to detect the tissue temperature while the ultrasound transducer assembly is transmitting the focused ultrasound beam to the target heating site.

15. The system of claim 12, wherein the ultrasound transducer assembly is configured to detect the tissue temperature.

16. The system of claim 15, further comprising a controller configured to detect the tissue temperature with thermal strain imaging.

17. The system of claim 12, further comprising a temperature sensor comprising at least one of an infrared sensor, a thermocouple sensor, or a thermistor sensor, configured to detect the tissue temperature.

18. The system of claim 17, wherein the temperature sensor is coupled to the shaft.

19. The system of claim 4, further comprising a controller configured to determine a location of the target treatment site or the target heating site within the nasal cavity with the ultrasound transducer assembly or a second ultrasound transducer assembly coupled to the shaft.

20. A system for treating a nasal condition, the system comprising:
  a probe including a shaft and a cryotherapy element coupled to the shaft, wherein the probe is configured to be advanced into a nasal cavity and to cryoablate treatment tissue including at least one nasal nerve at a target treatment site with the cryotherapy element;
  a temperature sensor configured to detect a tissue temperature; and
  a warming probe configured to be inserted into at least one of the nasal cavity to warm a non-treatment tissue to protect the non-treatment tissue from effects of cold temperature produced during cryoablation of the treatment tissue, wherein warming the non-treatment tissue comprises warming target heating sites identified based upon the temperature sensor detecting the tissue temperature around the target treatment site during cryoablation of the treatment tissue.

21. The system of claim 20, wherein the warming probe includes a laser assembly configured to transmit a laser beam to the non-treatment tissue.

* * * * *